United States Patent [19]

Thuillier et al.

[11] 4,207,319
[45] Jun. 10, 1980

[54] THIENYL OR FURYL PHENYL O-HETERO AMINO ALKYL OXIMES AND USE THEREOF

[75] Inventors: Germaine Thuillier, Paris; Jacqueline Laforest, Vincennes; Pierre Bessin, Chilly Mazarin, all of France

[73] Assignee: Albert Rolland S.A., Paris, France

[21] Appl. No.: 896,621

[22] Filed: Apr. 14, 1978

Related U.S. Application Data

[60] Continuation-in-part of Ser. No. 804,777, Jun. 8, 1977, abandoned, which is a division of Ser. No. 515,063, Oct. 15, 1974, Pat. No. 4,029,808.

[30] Foreign Application Priority Data

Oct. 19, 1973 [FR] France .................................. 73 37444

[51] Int. Cl.$^2$ ................. C07D 413/12; C07D 405/12; A61K 31/535; A61K 31/40
[52] U.S. Cl. ......................... 424/248.51; 424/248.56; 424/250; 424/274; 424/275; 424/285; 544/146; 544/152; 544/379; 260/326.5 D; 260/326.5 SM; 260/326.84; 260/330.3; 260/347.7
[58] Field of Search ................... 544/146, 152, 379; 260/326.5 D, 326.5 SM, 326.84, 329 AM, 332.3 R, 347.7; 424/248.51, 248.56, 274, 250, 267, 274, 275, 285

[56] References Cited

U.S. PATENT DOCUMENTS 4,029,808    6/1977    Thuillier et al. ..................... 424/275

OTHER PUBLICATIONS

Kurihara et al. "Chem. Abstracts," vol. 87 (1977) No. 134481n, Abstract of Japanese Patent 7,641,620, 11-1-1-76; Chemical Substance Index, vol. 87 (1977) p. 3356cs.

*Primary Examiner*—Henry R. Jiles
*Assistant Examiner*—R. W. Ramsuer

[57] ABSTRACT

Aromatic compounds having the following formula are disclosed:

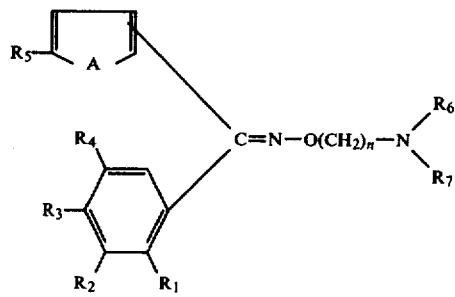

in which,
A in the heterocyclic group is selected from the group of O and S;
$R_1$, $R_2$, $R_3$ and $R_4$, which may be identical or different, are selected from the group consisting of hydrogen, halogen, lower alkyl, lower alkoxy;
$R_5$ is selected from the group consisting of hydrogen, lower alkyl and nitro;
n is an integer from 1 to 3 and
$R_6$ and $R_7$ together with the nitrogen atom to which they are attached form a 5- to 7-membered N-heterocyclic saturated group which optionally contain a second hetero atom, which may be O or N and pharmaceutically acceptable acid addition salts of the amino group thereof, said compound being in the form of the E isomer of the oximino group, the Z isomer or mixtures thereof.

These novel compounds exhibit a coronary vasodilatory activity and may be used in the treatment of cardiopathies.

A method of treating such disorders and a composition useful for treating same are also disclosed.

5 Claims, No Drawings

THIENYL OR FURYL PHENYL O-HETERO AMINO ALKYL OXIMES AND USE THEREOF

This application is a continuation-in-part of Ser. No. 804,777 filed June 8, 1977, abandoned, which in turn is a divisional of Ser. No. 515,063 filed Oct. 15, 1974 (now U.S. Pat. No. 4,029,808).

The invention relates to aromatic compounds having the formula

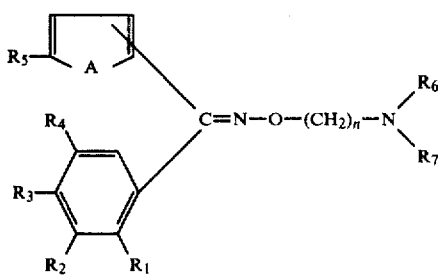

in which
A in the heterocyclic group is selected from the group of O and S $R_1$, $R_2$, $R_3$, $R_4$ which may be identical or different are selected from the group consisting of hydrogen, halogen, alkyl containing 1,2,3 or 4 carbon atoms, alkoxy group containing 1,2,3 or 4 carbon atoms and alkenyloxy.

$R_5$ is selected from the group consisting of hydrogen alkyl containing 1,2,3, or 4 carbon atoms and nitro n is 1,2 or 3 and $R_6$ and $R_7$ together with the nitrogen atom to which they are attached form a 5,6 or 7 membered N-heterocyclic saturated group which may contain a second hetero atom which may be O, or N and pharmaceutically acceptable acid addition salts thereof, said compound being in the form of the cis isomer, trans isomer or mixture thereof.

These novel chemical compounds have very important pharmacological properties. They have been shown to have a coronary vasodilatatory activity, to slow down the heart rate and to reduce the diastolic pressure and to protect animals against digitalis poisoning. These products, which have a completely original therapeutic action, may so be used beneficially in the treatment of cardiopathics. The invention also proposes therapeutic compositions which can be administered orally or parenterally and which contain, as active ingredient, at least one of the geometric isomers of the oxime ethers of formula I or one of their pharmaceutically acceptable acid addition salts in combination with an excipient therefor. The unit dose for oral administration is 1 to 100 mg and for parenteral administration 1 to 50 mg. The number of daily doses varies according to the nature of the case under treatment.

Process for the preparation of compounds of formula I comprises a diaromatic ketone of the formula (II)

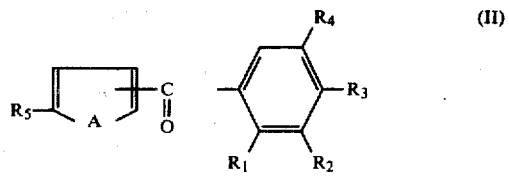

wherein A, $R_1$, $R_2$, $R_3$, $R_4$ and $R_5$ are as defined for formula I, which is reacted with a hydroxylamine of the formula $H_2N$—O—R wherein R is the hydrogen atom or the group $(CH_2)_n$—$NR_6R_7$ wherein n, $R_6$ and $R_7$ are as defined for formula I; and when R is $(CH_2)_n$—$NR_6R_7$, the reaction is carried out in an alcoholic or aqueous alcoholic solvent in an acidic medium and when R is H the reaction is carried out in pyridine under reflux and the intermediate compound thereby obtained is reacted in the presence of a base with a compound of the formula X—$(CH_2)_n$—$NR_6R_7$ wherein X, $R_6$, $R_7$ are as defined for formula I. A mixture of the two geometric isomers of the oximino group is obtained in all cases.

The acid addition salts of the amino group are prepared by the action of a mineral or organic acid on the compounds thus obtained. The acid used may be, in particular, a hydrohalic acid, fumaric acid, maleic acid, mathanesulphonic acid or glycollic acid.

The two geometric isomers of these oxime ethers are difficult to separate when the amine function has not been salified. The differences in solubility of the acid addition salts enables separation to be achieved by successive recrystallisations.

Further advantages and characteristics of the invention will be better understood with the aid of the examples of preparation given below which are in no way limiting but given by way of illustration. The melting points mentioned in the examples were determined on a kofler block.

When the two geometric isomers of these oximes were not separated, their relative proportions in the mixture were determined by studying their nuclear magnetic resonance spectra.

EXAMPLE 1

(2,3-dichloro-4-methoxy)phenyl 2-thienyl O-(morpholinoethyl)methanone oxime

A solution of 10 g of (2,3-dichloro-4-methoxy) phenyl 2-thienyl methanone and 7,5 g of morpholinoethoxyamine, dihydrochloride (m.p. = 190° C. after recrystallisation from aqueous ethanol 95%) in 100 ml of ethanol is kept at its reflux temperature during 4 hours. The solvent is removed under reduced pressure. 150 ml of water are poured on the residue and the unreacted ketone extracted in benzene. The final product is extracted in diethyl ether from the aqueous solution after alcalinisation. 4 g of the mixture of the two geometric isomers are obtained.

The amine hydrochloride of the Z isomer which has the cis configuration in relation to thiophene, after recrystallisation from ethanol melts at 237° C.

EXAMPLE 2

(2,3-dichloro-4-methoxy)-phenyl 2-furyl O-(1-pyrrolidinyl-ethyl)-methanone oxime Applying the method described in Example 1, 12 g of a mixture of the two isomers of this oxime were obtained from 13.55 g of (2,3-dichloro-4-methoxy)-phenyl 2 furyl methanone and 10.15 g of O-(1-pyrrolidinyl-ethyl-hydroxyl amine dihydrochloride (m.p. = 150° C. after recrystallisation from ethanol).

The mixture of amine hydrochlorides consisting of 30% of the Z geometric isomer of the oxime (in the cis configuration in relation to the heterocyclic group) and 70% of the E isomer melts at 161° C.

EXAMPLE 3

(2,3-dichloro 4-methoxy)phenyl 2-furyl O-(4-methy piperazinyl-propyl) methanone oxime

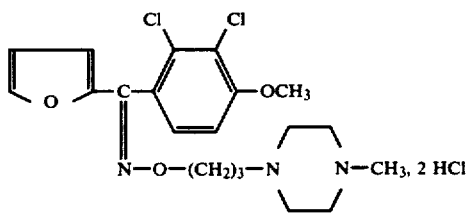

A. In 200 ml of pyridine are dissolved 100 g of (2,3-dichloro 4-methoxy)phenyl 2-furyl methanone and 100 g of hydroxyl-amine hydrochloride. The mixture is maintained 3 hours at reflux temperature, and then the solvent eliminated under reduced pressure. Water and hydrochloric acid are introduced, and then diethylether. The organic phase decanted. After usual treatments 97 g of oxime, melting at 172° C., are isolated, as a mixture of the two geometric isomers.

B. In 100 ml of dimethylformamide are dissolved 7,5 g of oxime obtained under A above; 5 g of 4-methyl 1-[3-chloro]-peopyl piperazine and 4 g of anhydrous potassium carbonate are added; the mixture is maintained 15 hours at 50° C. about. The solid is excluded, the solvent evaporated and the mixture poured into water. The final product extracted and purified by dissolution in acidic water. It is obtained as dihydrochloride by action of hydrochloric acid on the amine in ethanol solution. Yield: 41%. Analytically pure, the mixture of the two isomers (40% of (E) isomer) melts at 218° C. Isomer E is of trans type.

Some other compounds of formula and physical properties of these compounds are given in the following table.

TABLE I

| Ex. | Structural Formula | % (E) isomer | F.° C. |
|---|---|---|---|
| 4 | (structure: 2,3-dichloro-4-methoxyphenyl 2-furyl C=N—O—(CH₂)₂—N[piperazinyl]N—CH₃, 2 HCl) | 65 | 238 |
| 5 | (structure: 2,3-dichloro-4-methoxyphenyl 2-furyl C=N—O—(CH₂)₂—N[hexamethyleneimino], HCl + H₂O) | 100 | 152 |
| 6 | (structure: 2,3-dichloro-4-methoxyphenyl 2-furyl C=N—O—(CH₂)₂—N[morpholino]) | 100 | 174 |
| 7 | (structure: 2,3-dimethyl-4-methoxyphenyl 2-thienyl C=N—O—(CH₂)₂—N[morpholino]) | 100 | 195 |
| 8 | (structure: 2,3-dichloro-4-methoxyphenyl 2-thienyl C=NO—(CH₂)₂—N[pyrrolidinyl], HCl) | 30 | 108 |

The compounds of the invention, in the form of their acid addition salts, have been the object of a toxicological and pharmacological study which has shown their therapeutic importance.

The two geometric isomers of the oxime ethers of formula I have similar pharmacological activities but with differing intensities.

The acute toxicity was determined on mice; the $DL_{50}$ of all products, administered per os, is greater than 1 g/kg.

These compounds have an antispasmodic activity which was demonstrated in vitro on a isolated organ. A loop of rat duodenum kept alive in an aerated bath of 50 ml of tyrode solution at a temperature of 38° C. is contracted periodically by the addition of a solution of barium chloride. The products under investigation were added to the solution to determine the concentration required to produce 50% inhibition of the contractions. All the compounds showed an activity at least comparable to that of papaverine hydrochloride.

The cardiac activity of the products according to the invention was studied in the anaesthetized dog: Cardiac rhythm, arterial pressure at the level of the carotid artery, variations in coronary vasomotor activity determined by an electromagnetic flow meter, and the variation with time of the elevation in pressure of the left endocavitory or intra-aortic blood medium were recorded. The following effects were noticed: Bradycardiac activity slowing down of cardiac rhythm being proportional to the dose injected, were observed after administration of the compounds, and pronounced coronary vasodilatory activity which, taking into account the toxicity of the compounds, was distinctly superior to that of papaverine hydrochloride; the $ED_{50}$ of all the products, calculated for coronary vasodilatory activity, is about 10 mg/kg (after intravenous administration).

The compounds prevent also the animals from the cardiac effects of digitalis poisoning.

We claim:

1. An aromatic compound having the formula:

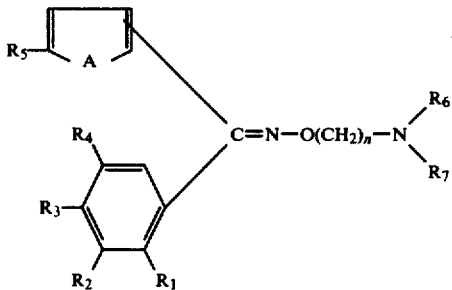

in which,

A in the heterocyclic group is selected from the group of O and S;

$R_1$, $R_2$, $R_3$ and $R_4$, which may be identical or different, are selected from the group consisting of hydrogen, halogen, lower alkyl, lower alkoxy;

$R_5$ is selected from the group consisting of hydrogen, lower alkyl and nitro;

n is an integer from 1 to 3 and $R_6$ and $R_7$ together with the nitrogen atom to which they are attached form a morpholino, pyrrolidino, N-methyl piperazino or hexahydroazepino group and pharmaceutically acceptable acid addition salts of the amino group thereof, said compound being in the form of the E isomer of the oximino group, the Z isomer or mixture thereof.

2. The compound according to claim 1 in which said oxime is the E isomer.

3. The compound according to claim 1 in which said oxime is the Z isomer.

4. A method inducing coronary vasodilatory activity which comprises administering orally or parenterally to a patient in need thereof a therapeutically effective amount of at least one compound according to claim 1.

5. A composition useful for inducing coronary vasodilatory activity which comprises a therapeutically effective amount of a compound according to claim 1 and a physiologically acceptable excipient therefor.

* * * * *